United States Patent [19]
Sze et al.

[11] 3,939,209
[45] Feb. 17, 1976

[54] ACETALDEHYDE PRODUCTION

[75] Inventors: Morgan C. Sze, Upper Montclair; Ruey H. Wang, Parsippany, both of N.J.

[73] Assignee: The Lummus Company, Bloomfield, N.J.

[22] Filed: Feb. 24, 1975

[21] Appl. No.: 552,534

Related U.S. Application Data

[62] Division of Ser. No. 183,788, Sept. 27, 1971, Pat. No. 3,869,518.

[52] U.S. Cl. ...................... 260/604 AC; 260/659 A
[51] Int. Cl.$^2$......................................... C07C 45/04
[58] Field of Search ................. 260/604 AC, 497 A

[56] References Cited
FOREIGN PATENTS OR APPLICATIONS
1,952,781  6/1970  Germany..................... 260/604 AC

*Primary Examiner*—James O. Thomas, Jr.
*Assistant Examiner*—R. H. Liles
*Attorney, Agent, or Firm*—Marn & Jangarathis

[57] ABSTRACT

Acetaldehyde is produced from ethane by contacting ethane in the absence of added chlorine or hydrogen chloride with a molten mixture of the higher and lower valent form of a multivalent metal chloride and the oxychloride of the metal, such as a mixture of cuprous chloride, cupric chloride and copper oxychloride, in the presence of ethylene and ethyl chloride and optionally also vinyl chloride. Acetaldehyde is produced with no net production of ethyl chloride and ethylene, and if vinyl chloride is present, no net production of vinyl chloride.

16 Claims, 2 Drawing Figures

ACETALDEHYDE PRODUCTION

This is a division of application Ser. No. 183,788, filed Sept. 27, 1971 now U.S. Pat. No. 3,869,518.

This invention relates to the production of acetaldehyde. This invention further relates to the production of both acetaldehyde and vinyl chloride.

Acetaldehyde is generally produced by the oxidation of ethylene in the presence of a noble metal catalyst. Ethylene is a relatively expensive material, and it would be desirable to provide a process which is capable of producing acetaldehyde from ethane and/or ethylene.

An object of this invention is to provide a new and improved process for producing acetaldehyde.

Another object of this invention is to provide a process for producing acetaldehyde from ethane and/or ethylene.

Figure 1:
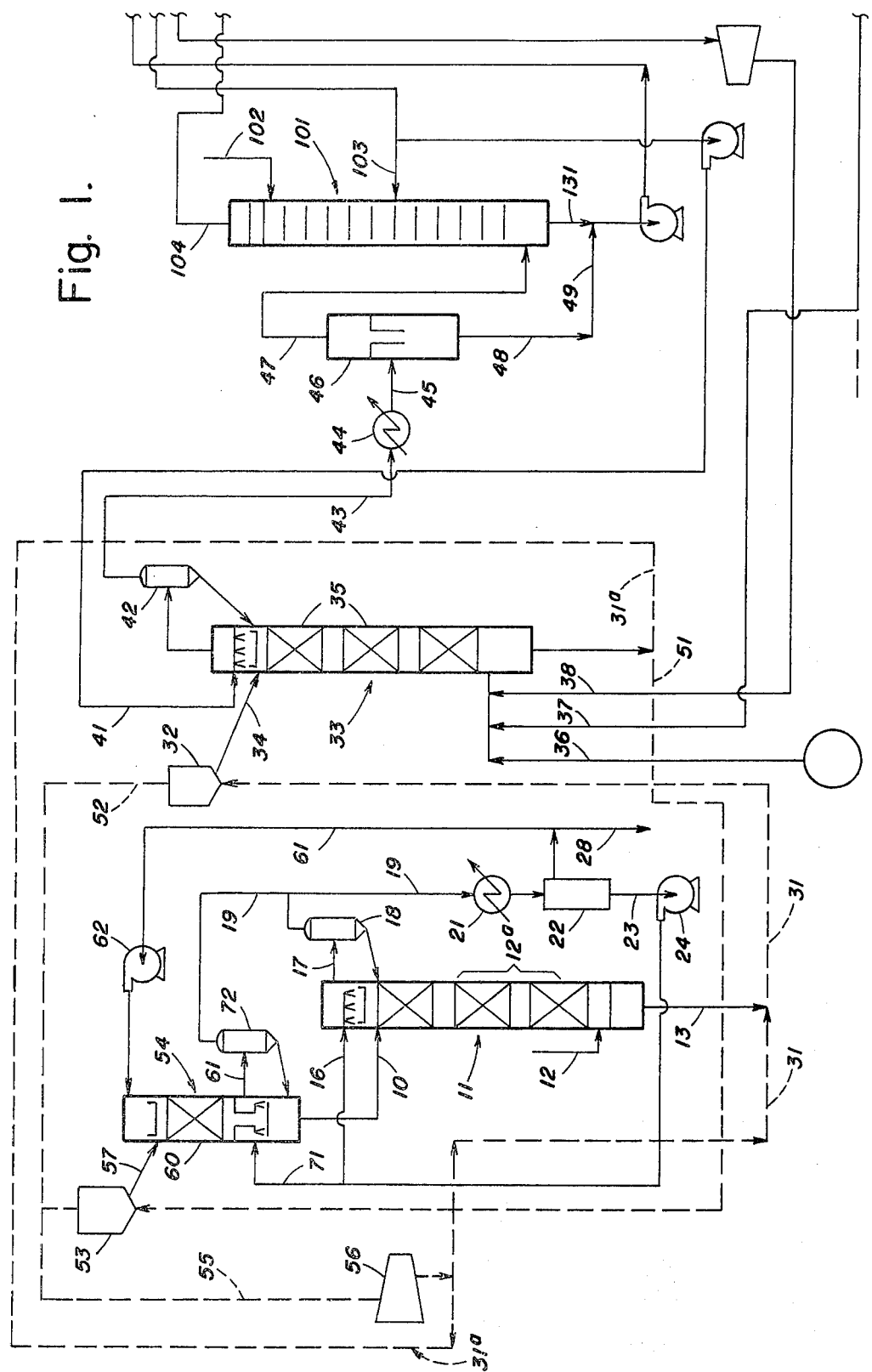
Figure 2:
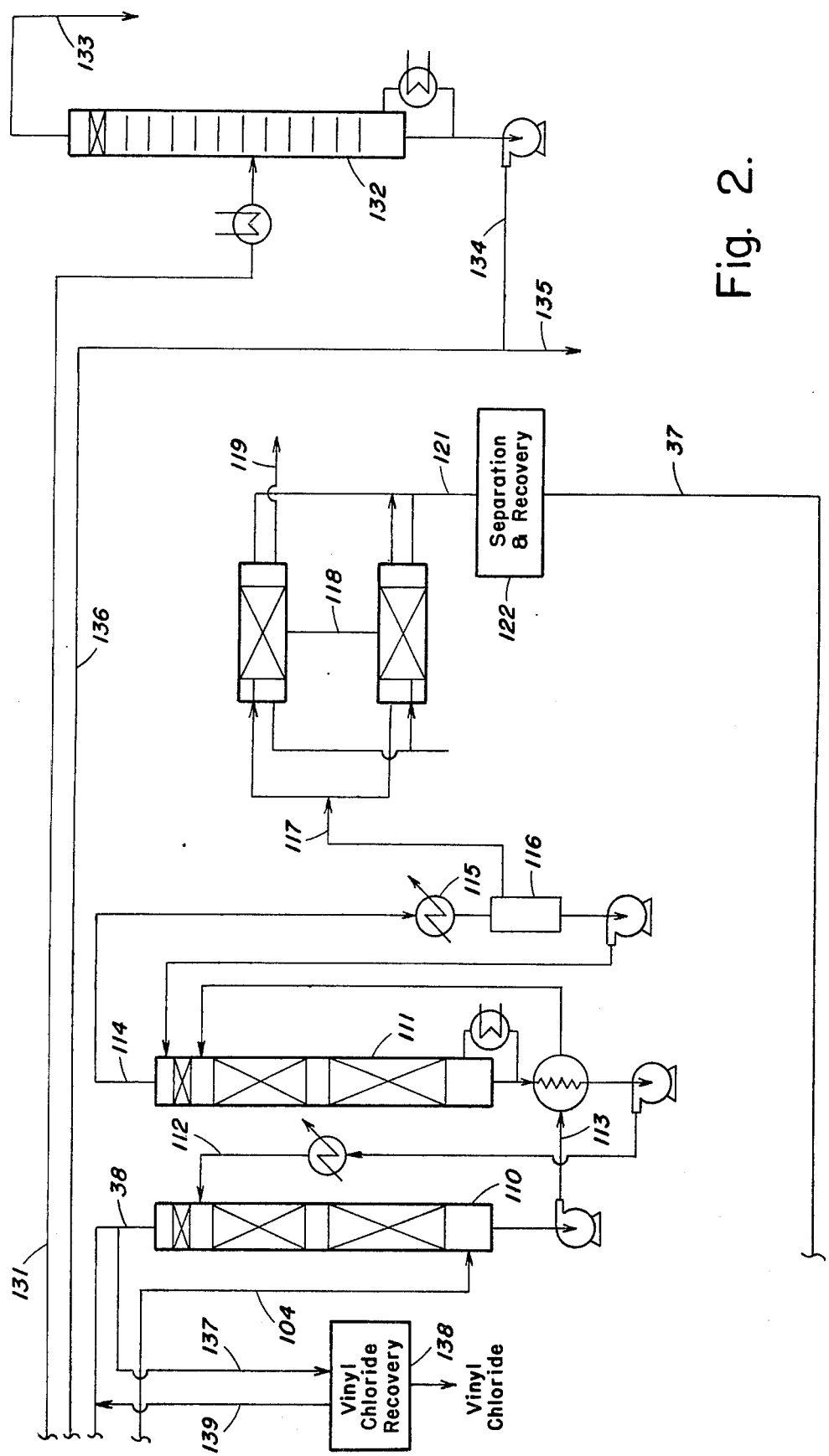

These and other objects of the invention should be more readily apparent from reading the following detailed description thereof with reference to the accompanying drawings wherein:

FIG. 1 is a simplified schematic flow diagram of a portion of an embodiment of the present invention; and FIG. 2 is a simplified schematic flow diagram completing the embodiment of FIG. 1.

The objects of this invention are broadly accomplished by contacting a molten mixture of a multivalent metal chloride, in both its higher and lower valence state, and the oxychloride of the metal, with a gaseous feed of ethane and/or ethylene and either ethyl chloride or a mixture of ethyl chloride and vinyl chloride, the contacting being effected in the substantial absence of added chlorine or hydrogen chloride, to produce a reaction effluent which includes acetaldehyde. It has been found that the inclusion of ethyl chloride in the feed results in no net production of ethyl chloride from the ethane and/or ethylene. Similarly, the inclusion of vinyl chloride results in no net production of vinyl chloride from the ethane and/or ethylene. Accordingly, in accordance with the invention, acetaldehyde can be produced with essentially no net production of ethyl chloride and also, if desired, with essentially no net production of vinyl chloride.

The melt contains a chloride of a multivalent metal; i.e., a metal having more than one positive valence state, such as manganese, iron, copper, cobalt, and chromium, preferably copper. In the case of higher melting multivalent metal chlorides, such as copper chlorides, a metal salt melting point depressant which is non-volatile and resistant to the action of oxygen at the process conditions, such as a chloride of a univalent metal i.e., a metal having only one positive valence state, is added to the multivalent metal chloride to form a molten salt mixture having a reduced melting point. The univalent metal chlorides, are preferably alkali metal chlorides, such as potassium and lithium chloride in particular, but it is to be understood that other metal chlorides and mixtures thereof, such as the heavy metal chlorides i.e., heavier than copper, of Groups I, II, III and IV of the Periodic Table; e.g., zinc, silver, and thallium chloride, may also be employed. The metal chloride melting point depressant is added in any amount sufficient to maintain the salt mixture as a melt at the reaction temperatures, and is generally added in an amount sufficient to adjust the melting point of the molten salt mixture to a temperature of below about 500°F. In the case of a salt mixture of copper chlorides and potassium chloride, the composition of the melt ranges from about 20% to about 40%, preferably about 30%, by weight, potassium chloride, with the remainder being copper chlorides. It is to be understood, however, that in some cases the catalyst melt may have a melting point higher than 500°F., provided the catalyst remains in the form of the melt throughout the processing steps. It is further to be understood that the melt may contain a mixture of multivalent metal chlorides or other reaction promoters. It is also to be understood that in some cases, metal chloride may be maintained as a melt without the addition of a metal halide melting point depressant.

In accordance with one embodiment of the present invention, acetaldehyde is produced with no net production of vinyl chloride or ethyl chloride by including both vinyl chloride and ethyl chloride in the feed to the acetaldehyde production reactor. The overall reaction may be represented by the following equations:

1. $C_2H_6 + O_2 \rightarrow C_2H_4O + H_2O$
2. $C_2H_4 + \frac{1}{2}O_2 \rightarrow C_2H_4O$ The oxygen requirements of the process are provided by the oxychloride of the molten mixture.

The oxychloride which is used in the acetaldehyde production reactor may be generated, in situ, by including, as feed to the reactor, a molecular oxygen-containing gas, but in general, such a procedure is not preferred. In accordance with the preferred procedure, the molten salt is contacted in a separate reaction zone with a molecular oxygen-containing gas to produce copper oxychloride, as represented by the following equation, using copper chlorides as a representative salt:

3. $2CuCl + \frac{1}{2}O_2 \rightarrow CuO \cdot CuCl_2$

The molten salt, containing the copper oxychloride is then employed in the acetaldehyde production reactor. In this manner, there is no direct contact between the molecular oxygen-containing gas and the hydrocarbon feed.

In accordance with another embodiment of the invention, vinyl chloride is produced as a co-product with the acetaldehyde. The overall reaction for the production of vinyl chloride may be represented by one or more of the following equations:

4. $C_2H_6 + \frac{1}{2}Cl_2 + \frac{3}{4}O_2 \rightarrow C_2H_3Cl + 3/2H_2O$
5. $C_2H_6 + HCl + O_2 \rightarrow C_2H_3Cl + 2H_2O$
6. $C_2H_4 + \frac{1}{2}Cl_2 + \frac{1}{4}O_2 \rightarrow C_2H_3Cl + \frac{1}{2}H_2O$
7. $C_2H_4 + HCl + \frac{1}{2}O_2 \rightarrow C_2H_3Cl + H_2O$ As hereinabove noted, no hydrogen chloride and chlorine are added to the acetaldehyde production reactor in that the presence of such components adversely effects the production of the desired acetaldehyde product and, accordingly, the chlorine requirements for the vinyl chloride production are provided by the molten salt mixture; in particular, the higher valent metal chloride, as represented by the following equation, using cupric chloride as a representative example:

8. $2CuCl_2 \rightarrow 2CuCl + Cl_2$

It should be readily apparent that this would result in a continuous depletion of the higher valent metal chloride; i.e., cupric chloride and, consequently, the molten mixture must be enriched with the higher valent metal chloride.

In accordance with the embodiment of the invention in which vinyl chloride is desired as a co-product, the molten salt is contacted in a first reaction zone with molecular oxygen and hydrogen chloride and/or chlorine in an amount sufficient to provide both the chlorine requirements and the oxygen requirements for the production of vinyl chloride and acetaldehyde, as represented by the following equations:

9. $2CuCl + Cl_2 \rightarrow 2CuCl_2$
10. $2CuCl + 2HCl + \frac{1}{2}O_2 \rightarrow 2CuCl_2 + H_2O$
11. $2CuCl + \frac{1}{2}O_2 \rightarrow CuO \cdot CuCl_2$ Thus, the molten salt mixture is enriched in cupric chloride to provide the chlorine requirements for the production of vinyl chloride, and is also enriched in copper oxychloride to provide the oxygen requirements for the production of acetaldehyde.

The production of acetaldehyde is effected by contacting the molten salt and hydrocarbon feed at temperatures from about 700°F. to about 1000°F., preferably from about 800°F. to about 875°F. and at pressures from about 1 atm. to about 15 atm., preferably from about 2 atm. to about 10 atm. The contacting of the feed and melt is generally effected in a countercurrent fashion, preferably with the feed as a continuous vapor phase, at residence times from about 1 to about 60 seconds. In the preferred embodiment of the invention, wherein the molten salt mixture is previously contacted with a molecular oxygen-containing gas, in a separate reactor, such contacting is generally effected at temperatures from about 700°F. to about 1000°F., preferably from about 750°F. to about 950°F.

It should be apparent from the hereinabove noted reaction sequences, that the melt containing the multivalent metal chloride, in some cases, participates in the reaction sequence and accordingly does not behave only as a catalyst. Thus, for example, the melt functions to transfer oxygen, and as should be apparent from the hereinabove noted equations, sufficient oxychloride must be produced to provide the oxygen requirements for the reactions, such requirements being greater for ethane as compared to ethylene. In general, the oxychloride content of the molten mixture introduced into the acetaldehyde production reactor ranges from about 1% to about 5.5%, and preferably from about 1.5% to about 4%, all by weight, of the melt. It should be apparent that lower amounts of oxychloride can be employed, but such lower amounts reduce conversion or necessitate the use of high salt to feed circulation rates to maintain conversion.

The melt, in addition to functioning as a reactant and/or catalyst is a temperature regulator. Thus, the circulating melt has a high heat absorption capacity, thereby preventing runaway reaction during the exothermic oxidation. The absorbed heat of reaction may be employed to heat the various reactants to reaction temperature. It should be apparent, however, that if additional heating or cooling is required, such heating or cooling may be supplied from an external source. It should also be apparent that the heat absorption capacity of the melt functions to limit temperature variations, i.e., temperature gradients, during the reactions.

Thus, as should be apparent from the hereinabove description of the present invention, acetaldehyde may be produced from ethane and/or ethylene by contacting thereof with a molten mixture containing the higher and lower valent forms of a multivalent metal chloride and the oxychloride of the metal, in the absence of added chlorine and hydrogen chloride, and in the presence of ethyl chloride and optionally also in the presence of vinyl chloride if no net production of vinyl chloride is desired.

In accordance with a preferred embodiment of the invention, acetaldehyde is produced from ethane using copper chlorides as the molten salt mixture. The acetaldehyde may be produced, if desired, with a net production of vinyl chloride, as a co-reaction product, or with no net production of vinyl chloride. In accordance with this preferred embodiment, ethyl chloride is introduced into the production reactor and there is no net production of ethyl chloride. In addition, ethylene is introduced into the acetaldehyde production reactor and there is no net production of ethylene.

The molten salt mixture, preferably containing from about 20% to about 40% potassium chloride, as a melting point depressant, and from about 15% to about 30% cupric chloride with the remainder being cuprous chloride, all by weight, based on the three components, is contacted in a first reactor with molecular oxygen to produce copper oxychloride. The molecular oxygen is preferably introduced in an amount, and at a rate, to provide a molten salt mixture containing from about 1.5% to about 4%, all by weight, of copper oxychloride. It is to be understood that chlorine and/or hydrogen chloride could also be introduced into the first reactor as hereinabove described to enrich the salt in cupric chloride for producing vinyl chloride as a co-reaction product.

The molten salt mixture, containing copper oxychloride, in the amounts hereinabove specified, is circulated to a second reactor (acetaldehyde production reactor) wherein the molten salt is contacted with ethane, as fresh feed, ethyl chloride, ethylene and recycle unconverted ethane. In addition, if no net production of vinyl chloride is desired, the feed to the second reactor includes vinyl chloride. The feed to the second reactor does not include hydrogen chloride and/or chlorine in that such components reduce and/or eliminate the production of acetaldehyde. The ethyl chloride is generally introduced in an amount to provide an ethyl chloride to fresh feed ethane ratio from about 1:1 to about 10:1, preferably from about 3:1 to about 7:1. The vinyl chloride, if present, is introduced in an amount to provide a vinyl chloride to fresh feed ethane weight ratio from about 1:1 to about 10:1, preferably from about 2:1 to about 7:1. The ethylene is generally introduced into the second reactor in an amount to provide an ethylene to fresh feed ethane weight ratio from about 0.5:1 to about 5:1, preferably from about 1:1 to about 2.5:1. The molten salt to fresh feed ethane weight ratio generally ranges from about 2500:1 to about 350:1, with the molten salt functioning as a heat sink to prevent runaway exothermic reaction.

The effluent from the second reactor includes acetaldehyde, acetic acid, unconverted ethane, ethylene, vinyl chloride and ethyl chloride. In addition, the effluent includes carbon oxides, i.e., carbon dioxide and/or carbon monoxide, and some methane. The effluent may also include minor quantities of other chlorinated hydrocarbons, such as dichloroethylenes and dichloroethanes. The effluent is passed to a separation and recovery zone to recover acetaldehyde and acetic acid as reaction products, and recovered ethyl chloride and ethylene are returned to the second reactor to prevent net production of such components. If vinyl chloride is not desired as a reaction product, the recovered vinyl chloride is also recycled to the second reactor to prevent net production of vinyl chloride. The unconverted ethane is recovered and recycled to the second reactor for ultimate conversion to acetaldehyde.

It should be readily apparent that in accordance with the preferred embodiment, acetaldehyde is effectively produced from ethane and oxygen, or acetaldehyde and vinyl chloride are produced from ethane, oxygen and chlorine and/or hydrogen chloride, with no net production of ethyl chloride or ethylene.

It is to be understood that the preferred ethane feed could also contain some ethylene, as for example, in the case where a $C_2$ stream is recovered from a refinery.

The invention will be further described with respect to an embodiment thereof illustrated in the drawings. It is to be understood, however, that the scope of the invention is not to be limited thereby. It is further to be undnderstood that the molten chloride salts are highly corrosive and, accordingly, the processing equipment must be suitably protected; e.g., the reactors may be lined with ceramic. Similarly, if pumps are used for transporting the molten salts they must also be protected. The molten salts, however, are preferably transferred between the reactors by the use of gas lifts, as known in the art.

Referring now to FIG. 1, a molten chloride salt such as a mixture of potassium chloride, cupric and cuprous chloride in line 10 at a temperature of from 600°F. to 900°F. is introduced into the top of an oxidation vessel 11 maintained at a pressure of from about 1 to about 15 atms. A compressed oxygen-containing gas, such as air, in line 12 is introduced into the bottom of vessel 11 and is passed in countercurrent contact to the descending molten salt. The vessel 11 may be provided with one or more sections of packing, generally indicated as 12a, to promote intimate and effective contact between the compressed gas and molten salt. The molten salt is oxidized to produce oxychlorides, with the concurrent evolution of heat. The residence time of the molten salt within the vessel 11 is from about 1 to about 60 seconds.

The effluent gas leaving the packing near the top of vessel 11 is at a temperature of from about 600°F. to 900°F., and is contacted with a spray of a suitable quench liquid in line 16 to cool the effluent to a temperature of about 200°F. to 400°F. A suitable quench liquid would be aqueous hydrogen chloride. The gas is cooled by such contact with the result that vaporized and entrained salts are condensed and eliminated from the gas stream. The quench liquid spray is concurrently vaporized, and, together with the effluent gas, is withdrawn from the top of vessel 11. The total gaseous effluent is passed through line 17 to a cyclone separator 18 for the elimination of any solid material which is returned to the vessel 11. The gaseous effluent is thereafter combined with another gaseous effluent in line 19 as more fully hereinafter described. The combined gaseous effluent is cooled to about 100°F. to 150°F. in heat exchanger 21 to condense out the vaporized quench liquid. The condensed quench liquid is separated from the remaining gaseous effluent in vapor/liquid separator 22. The quench liquid is passed through line 23 by pump 24 with a portion being returned to the upper portion of vessel 11 through line 16. The gaseous effluent in separator 22 is divided with a portion being vented through line 28.

The molten salt, now containing the copper oxychloride, at a temperature of from about 700°F. to 1000°F. is withdrawn from the bottom of vessel 11 through line 13 and passed by a suitable lift gas such as nitrogen, in line 31 to a gas/liquid separator 32, adjacent the top of acetaldehyde production reactor 33 wherein the molten salt is separated from the lift gas. The molten salt in line 34 is introduced into the top of reactor 33. The reactor 33 is operated at a temperature of from about 700°F. to about 1000°F., at a pressure of from 1 to 15 atms., and a residence time of 1 to 60 seconds. The reactor 33 is provided with sections of packing, generally indicated as 35, designed to effect intimate and effective contact between the gaseous feed components and the molten salt as more fully hereinafter described.

Fresh ethane feed in line 36 is combined with a recycle gas, containing ethylene, unconverted ethane, vinyl chloride, ethyl chloride, some carbon oxides, water vapor and some methane, in line 38, and ethyl chloride in line 37, and the combined stream introduced into the bottom of reactor 33, wherein the combined stream countercurrently contacts the descending molten salt, resulting in the production of acetaldehyde, some acetic acid, carbon oxides (carbon dioxide and/or carbon monoxide) and some methane.

A gaseous effluent, containing acetaldehyde, acetic acid, carbon oxides, methane, unconverted ethane, ethylene, ethyl chloride, vinyl chloride and water vapor is contacted at the top of reactor 33 by a spray of suitable quench liquid from line 41 to effect cooling thereof to about 200°F. to about 400°F. to thereby separate entrained molten salt and resulting in vaporization of the quench liquid. A suitable quench liquid is aqueous acetic acid. The total gaseous effluent, including quench liquid is passed into cyclone separator 42 to remove molten salt and then is passed through line 43 and heat exchanger 44 wherein the effluent is cooled to ambient temperature. The cooled effluent in line 45 is introduced into a gas/liquid separator 46 to separate condensed quench liquid therefrom. The gas withdrawn from separator 46 in line 47 is passed to a separation and recovery section, as hereinafter described. The liquid aqueous acetic acid withdrawn from gas/liquid separator 46 in line 48 is passed to a separation and recovery section as hereinafter described.

The molten salt withdrawn from the bottom of reactor 33 is at a temperature of from about 700°F. to about 1000°F., and is passed through line 51 by the lift gas in line 31a, obtained as hereinafter described, to a separator 53 adjacent the top of direct heat exchange vessel 54. The lift gas separated in separator 53 is combined with the lift gas separated in separator 32 and compressed in compressor 56 and circulated through lines 31 and 31a for lifting the molten salt to the top of reactors 11 and 33, respectively. The molten salt from separator 53 in line 57 is introduced into heat exchange vessel 54 which comprises one or more packed sections, generally indicated as 60. A portion of the gas withdrawn from separator 22 is passed through line 61 compressed by gas blower 62, and introduced into the top of heat exchange vessel 54 wherein the compressed gas is passed in direct heat exchange contact with the molten salt inntroduced through line 57. The gas and the molten salt are concurrently passed over the packed sections 60 and are disengaged in the bottom of the heat exchange vessel 54. The gas is cooled by a spray of quench liquid introduced through line 71 to eliminate any vaporized or entrained halide salt. A gaseous effluent comprised of the gas introduced through line 61 and now vaporized quench liquid is withdrawn from vessel 54 and passed into cyclone separator 72. In separator 72 any solids are removed from the gaseous effluent. The gaseous effluent withdrawn from separator 72 is passed through line 19 and combined with the gaseous effluent from oxidation vessel 11. The combined gaseous effluent is passed through condenser 21 to condense the quench liquid. The principal purpose of the heat exchange vessel 54 is to bring the molten salt in line 10 to a constant and desired temperature prior to introducing the molten salt into the top of oxidation vessel 11. In general, the overall reaction provides a net exotherm and, therefore, cooling of the melt in vessel 54 is required.

The gas in line 47 is introduced into the bottom of an acetaldehyde scrubbing column 101, containing suitable gas/liquid contacting devices, to separate essentially all of the acetaldehyde and acetic acid from the gas. Fresh scrubbing liquid, such as demineralized water, is introduced into the top of scrubbing column 101 through line 102 and a lean aqueous acetic acid absorption solution is introduced into columun 101 through line 103. The column 101 is operated as known in the art to produce a gaseous overhead, essentially free of acetic acid and acetaldehyde.

A gaseous overhead, now essentially free of acetic acid and acetaldehyde from column 101 in line 104 is introduced into a carbon oxide separation zone, (FIG. 2) of a type known in the art, to separate carbon oxides, in praticular, carbon dioxide therefrom. A complete removal of carbon dioxide is not required; it only being necessary to remove the net carbon dioxide produced in reactor 33. As shown the carbon dioxide separation zone is comprised of an absorption tower 110 and a desorption tower 111 employing a suitable carbon dioxide absorption solution, such as a potassium carbonate solution. As known in the art, the gaseous stream in line 104 is countercurrently contacted in tower 110 with lean absorption solution introduced through line 112. An overhead, comprised of ethylene, unconverted ethane, vinyl chloride, ethyl chloride, any unabsorbed carbon oxides, water vapor and some methane is withdrawn from tower 111 through line 38 for recycle to reactor 33.

A rich absorption solution is withdrawn from tower 110 through line 113, heat exchanged against lean absorption solution from tower 111 and introduced into the top of tower 111 operated at conditions to desorb carbon dioxide from the absorption solution. A lean absorption solution is withdrawn from the bottom of tower 111 and introduced through line 112 into tower 110.

The desorbed carbon dioxide, which contains some ethyl chloride and water vapor, withdrawn from tower 111 through line 114, is cooled in condenser 115 to condense water therefrom. The condensed water is recovered in drum 116 and recycled to the top of tower 111 with make-up water.

The carbon dioxide from separator 116 in line 117, contains some ethyl chloride which is separated from the carbon dioxide stream in suitable adsorbers 118, containing an adsorbent such as activated charcoal, and the carbon dioxide vented to the atmosphere through line 119.

The adsorbers 118 are periodically reactivated by desorbing the ethyl chloride therefrom with steam and the steam-ethyl chloride mixture therefrom in line 121 is passed through a separation and recovery zone 122, containing a plurality of condensers and separators to recover the ethyl chloride therefrom. The recovered ethyl chloride is recycled to reactor 33 through line 37.

The rich absorption solution from tower 101 in line 131 is combined with the condensed aqueous acetic acid liquid in line 49 from separator 46, and the combined stream introduced into a fractional distillation column 132, operated at temperatures and pressures to recover specification grade acetaldehyde as overhead, which is withdrawn as product through line 133.

A dilute aqueous acetic acid bottoms is withdrawn from column 132 through line 134, and a primary portion thereof passed through line 136 for use in line 103 as lean absorption solution for tower 101 and as quench liquid in line 41 for reactor 33. A minor portion is passed through line 135 to recover acetic acid as product.

If vinyl chloride is desired as co-reaction product, the gas overhead from column 110 would be treated to separate vinyl chloride therefrom. Thus, for example, the gas overhead from column 110 is passed through line 137 to a vinyl chloride recovery zone 138, of a type known in the art, to recover vinyl chloride therefrom. For example, the gas could be contacted with an absorption solution for vinyl chloride, such as dichloroethanes, and the vinyl chloride enriched absorption solution heated at a low pressure to desorb vinyl chloride therefrom. The gas, now free of vinyl chloride, is returned to line 38 through line 139 for recycle to reactor 33. It is of course understood, as hereinabove described, that chlorine and/or hydrogen chloride would be introduced into reactor 11 to contact the molten salt and enrich the molten salt in cupric chloride to thereby maintain the chlorine balance.

Numerous modifications and variations of the described embodiment are possible in light of the above teachings. Thus, for example, the separation and recovery may be effected in a manner other than as particularly described.

Similarly, if ethyl chloride or ethylene is desired as a co-reaction product, such components may be recovered instead of recycled.

As a further alternative the direct heat exchange vessel could be eliminated and the temperature of the salt controlled by controlling the temperature of the lift gas.

These modifications and others should be apparent to those skilled in the art from the teachings herein.

The invention will be further described with respect to the following examples which further illustrate the invention but the scope of the invention is not to be limited thereby. Unless otherwise specified, all parts and proportions are by weight.

EXAMPLE I

A molten salt comprised of 30 wt% potassium chloride and 70 wt% of cuprous and cupric chloride is contacted in a first zone at a temperature of 850°F. and a pressure of 1 atm. with oxygen-enriched air containing 30–50 vol% oxygen to produce copper oxychloride.

The salt containing copper oxychloride is contacted in a second zone with the following feed and at the following conditions:

| | |
|---|---|
| Reaction Temperature: | 850°F. |
| Reaction Pressure: | 1.0 atmosphere |
| Reaction Time: | 5.0 sec. |
| Duration of Test: | 2.5 hours |
| GHSV: | 143 1/hr. |
| Process Feed: | |
|   Ethane | 300 cc/min. |
|   Ethylene | 20.8 " |
|   Vinyl Chloride | 16.7 " |
|   Ethyl Chloride | 22.4 " |

The per pass conversion of ethane is 4% and the selectivity is:

| | |
|---|---|
| Acetaldehyde | 70.9% |
| Acetic Acid | 1.2% |
| Carbon Dioxide | 23.5% |
| Carbon Monoxide | 3.0% |
| Methane | 1.4% |
| Total | 100.0% |

There is no net production of ethyl chloride, ethylene or vinyl chloride.

EXAMPLE II

The procedure of Example I is repeated with the conditions and feed in the second zone being as follows:

| | |
|---|---|
| Reaction Temperature: | 350°F. |
| Reaction Pressure: | 1.0 atmosphere |
| Reaction Time: | 4.8 sec. |
| Duration of Test: | 3.0 hours |
| GHSV: | 178 l/hr. |
| Process Feed: | |
| Ethane | 300 cc/min. |
| Ethylene | 15 " |
| Ethyl Chloride | 25 " |

The per pass conversion of ethane is 1.6%, and the selectivity is:

| | |
|---|---|
| Acetaldehyde | 28.2% |
| Acetic Acid | 7.2% |
| Vinyl Chloride | 23.7% |
| Carbon Dioxide | 36.9% |
| Methane | 4.0% |
| | 100.0% |

There is no net production of ethyl chloride or ethylene, but there is a net production of vinyl chloride in that there is no vinyl chloride present in the feed.

EXAMPLE III

The procedure of Example I is repeated except the temperature changed to 825°F., with the conditions and feed in the second zone being as follows:

| | |
|---|---|
| Reaction Temperature: | 825°F. |
| Reaction Pressure: | 1.0 atmosphere |
| Reaction Time: | 16.7 sec. |
| Duration of Test: | 3.0 hours |
| GHSV: | 43 l/hr. |
| Process Feed: | |
| Ethane | 100 cc/min. |
| Ethylene | 11.7 " |
| Vinyl Chloride | 13.8 " |
| Ethyl Chloride | 14.5 " |

The per pass conversion of ethane is 8% and the selectivity is:

| | |
|---|---|
| Acetaldehyde | 75.16% |
| Acetic Acid | 2.14% |
| Carbon Dioxide | 10.08% |
| Carbon Monoxide | 2.47% |
| Methane | 1.15% |
| Total | 100.0% |

There is no net production of ethyl chloride, ethylene or vinyl chloride.

The process of the present invention is particularly advantageous in that acetaldehyde can be produced from ethane. In the case where there is no net production of vinyl chloride, the selectivity to acetaldehyde should range from about 50% to about 80%, and the per pass conversion should range from 1.5% to about 12%. Although the process operates at low conversion and results in production of carbon oxides, which represents lost yield, the process is economically feasible as the result of the lower cost of ethane feed as compared to the cost of the ethylene feed required in prior art processes.

These advantages and others should be apparent to those skilled in the art from the teachings herein.

Numerous modifications and variations of the present invention are possible in light of the above teachings and, therefore, within the scope of the appended claims the invention may be practised in a manner other than as particularly described.

What is claimed is:

1. A process for producing acetaldehyde and vinyl chloride, comprising:

contacting a molten mixture comprising a multivalent metal chloride in both its higher and lower valence state and the corresponding oxychloride in an amount sufficient to provide oxygen requirements for acetaldehyde production, said multivalent metal being selected from the group consisting of copper, chromium, cobalt, maganese and iron with a gaseous feed comprising a hydrocarbon selected from the group consisting of ethane, ethylene and mixtures thereof and further comprising ethyl chloride in an amount sufficient to prevent net production thereof, said contacting being effected at a temperature from about 700°F to about 1000°F, in the essential absence of added chlorine and hydrogen chloride to produce a gaseous effluent comprising acetaldehyde and vinyl chloride.

2. A process for producing acetaldehyde and vinyl chloride, comprising:

contacting a molten mixture of a multivalent metal chloride in both its higher and lower valence state and the corresponding oxychloride, in an amount sufficient to provide oxygen requirements for acetaldehyde production, the multivalent metal being selected from the group consisting of copper, chromium, cobalt, maganese and iron with ethane and in addition, ethylene and ethyl chloride in an amount sufficient to prevent net production thereof in the essential absence of added chlorine and hydrogen chloride, said contacting being effected at a temperature from about 700°F to about 1000°F to produce a gaseous effluent comprising acetaldehyde.

3. A process for producing acetaldehyde and vinyl chloride, comprising:

a. contacting a molten mixture of cuprous chloride and cupric chloride with molecular oxygen to produce copper oxychloride and also with a member selected from the group consisting of chlorine, hydrogen chloride and mixtures thereof to enrich the cupric chloride content of the melt;

b. contacting the molten mixture from step (a) withe ethane as fresh feed and ethane, ethylene and ethyl chloride as recycle feed in an amount sufficient to prevent net production thereof said contacting being effected at a temperature from about 700°F to about 100°F in the essential absence of added chlorine and hydrogen chloride;

c. recovering from step (b) a gaseous effluent comprising acetaldehyde, vinyl chloride, ethane, ethylene and ethyl chloride;
d. recovering acetaldehyde and vinyl chloride from the gaseous effluent as reaction product;
e. recovering ethane, ethylene and ethyl chloride from the gaseous effluent as recycle feed to step (b); and
f. passing the molten mixture from step (b) to step (a).

4. The process of claim 1 wherein the multivalent metal chloride is copper chloride.

5. The process of claim 1 wherein the hydrocarbon is ethane.

6. The process of claim 5 wherein the molten mixture further comprises as a melting point depressant a metal chloride which is non-volatile and resistant to the action of oxygen to maintain the molten state at the reaction temperature.

7. The process of claim 6 wherein the melting point depressant is an alkali metal chloride.

8. The process of claim 5 wherein said gaseous effluent further comprises ethylene, ethyl chloride and unreacted ethane which are recovered and recycled to said contacting.

9. The process of claim 8 wherein the multivalent metal chloride is copper chloride.

10. The process of claim 8 wherein the molten mixture further comprises as a melting point depressant a metal chloride which is non-volatile and resistant to the action of oxygen to maintain the molten state at the reaction temperature.

11. The process of claim 5 wherein the ethyl chloride to ethane fresh feed weight ratio is from about 1:1 to about 10:1.

12. The process of claim 2 wherein the ethyl chloride to ethane fresh feed weight ratio is from about 1:1 to about 10:1 and the ethylene to ethane fresh feed weight ratio is from about 0.5:1 to about 5:1.

13. The process of claim 3 wherein the molten mixture further comprises as a melting point depressant a metal chloride which is non-volatile and resistant to the action of oxygen to maintain the molten state at the reaction temperature.

14. The process of claim 13 wherein the melting point depressant is potassium chloride.

15. The process of claim 14 wherein said cupric chloride comprises from about 15% to about 30%, by weight, of the molten mixture.

16. The process of claim 15 wherein the recycle ethyl chloride to feesh feed ethane weight ratio in step (b) ranges from about 1:1 to about 10:1; and the ethylene to fresh feed ethane weight ratio in step (b) ranges from about 0.5:1 to about 5:1.

* * * * *